United States Patent
Ito et al.

(10) Patent No.: US 10,925,526 B2
(45) Date of Patent: Feb. 23, 2021

(54) HEATING OXIMETER

(71) Applicant: Murata Manufacturing Co., Ltd., Nagaokakyo-shi, Kyoto-fu (JP)

(72) Inventors: Kinichi Ito, Nagaokakyo (JP); Hirofumi Tsuchimoto, Nagaokakyo (JP)

(73) Assignee: Murata Manufacturing Co., Ltd., Kyoto (JP)

( * ) Notice: Subject to any disclaimer, the term of this patent is extended or adjusted under 35 U.S.C. 154(b) by 243 days.

(21) Appl. No.: 15/919,261

(22) Filed: Mar. 13, 2018

(65) Prior Publication Data

US 2018/0199872 A1   Jul. 19, 2018

Related U.S. Application Data

(63) Continuation of application No. PCT/JP2016/075775, filed on Sep. 2, 2016.

(30) Foreign Application Priority Data

Sep. 14, 2015   (JP) .................................. 2015-180406

(51) Int. Cl.
*A61B 5/1455*   (2006.01)
*A61B 5/1491*   (2006.01)
*A61B 5/024*    (2006.01)

(52) U.S. Cl.
CPC ...... *A61B 5/14552* (2013.01); *A61B 5/02416* (2013.01); *A61B 5/1491* (2013.01)

(58) Field of Classification Search
None
See application file for complete search history.

(56) References Cited

U.S. PATENT DOCUMENTS

| | | | |
|---|---|---|---|
| 4,539,994 | A | 9/1985 | Baumbach et al. |
| 4,926,867 | A | 5/1990 | Kanda et al. |
| 5,131,391 | A | 7/1992 | Sakai et al. |
| 6,343,223 | B1 | 1/2002 | Chin et al. |
| 2007/0123756 | A1 | 5/2007 | Kitajima et al. |

(Continued)

FOREIGN PATENT DOCUMENTS

| | | |
|---|---|---|
| JP | 55-88750 A | 7/1980 |
| JP | 58-501659 A | 10/1983 |
| JP | 63-23645 A | 1/1988 |

(Continued)

OTHER PUBLICATIONS

Official Communication issued in International Patent Application No. PCT/JP2016/075775, dated Nov. 8, 2016.

*Primary Examiner* — Marjan Fardanesh
(74) *Attorney, Agent, or Firm* — Keating & Bennett, LLP

(57) ABSTRACT

A heating oximeter includes a heat insulation portion, a heat generation portion including a resistor generating heat by energization, a first temperature detector including a first temperature sensor detecting a temperature of the heat generation portion, an oxygen saturation acquisition assembly including light emitting elements and a light receiving element, and acquiring oxygen saturation in blood optically, and a third temperature detector including a third temperature sensor detecting a temperature of a living body. The heating oximeter is provided by stacking the third temperature detector, the oxygen saturation acquisition assembly, the first temperature detector, the heat generation portion, and the heat insulation portion in this order.

20 Claims, 7 Drawing Sheets

(56) References Cited

U.S. PATENT DOCUMENTS

2013/0060098 A1  3/2013  Thomsen et al.

FOREIGN PATENT DOCUMENTS

| JP | 03-23846 A | 1/1991 |
|---|---|---|
| JP | 2004-344368 A | 12/2004 |
| JP | 2007-020890 A | 2/2007 |
| JP | 2007-105316 A | 4/2007 |
| JP | 2013-515528 A | 5/2013 |

HEATING OXIMETER

CROSS REFERENCE TO RELATED APPLICATIONS

This application claims the benefit of priority to Japanese Patent Application No. 2015-180406 filed on Sep. 14, 2015 and is a Continuation Application of PCT Application No. PCT/JP2016/075775 filed on Sep. 2, 2016. The entire contents of each application are hereby incorporated herein by reference.

BACKGROUND OF THE INVENTION

1. Field of the Invention

Preferred embodiments of the present invention relate to a heating oximeter that measures oxygen saturation in blood while heating a measurement site.

2. Description of the Related Art

As an existing index of the amount of oxygen that is transported to a body, in particular, an index of whether or not sufficient oxygen can be supplied to the body involving the lungs, oxygen saturation ($SpO_2$) indicating a ratio of hemoglobin (oxygenated hemoglobin: $HbO_2$) which actually carries oxygen in hemoglobin in blood has been used. A pulse oximeter has been used in order to measure the oxygen saturation.

For example, Japanese Unexamined Patent Application Publication No. 63-23645 discloses a reflection heating oximeter that measures oxygen saturation in blood using an optical sensor in a bloodless manner and includes a light emitting portion outputting measurement light of two different wavelengths by the optical sensor, a light receiving portion receiving scattered/reflected light of the measurement light from a biological portion, and a heating unit capable of controlling a temperature around the light emitting portion and the light receiving portion.

The reflection heating oximeter can detect a pulsatile component and measure oxygen saturation by heating a measurement site by the heating unit capable of controlling the temperature and increasing a blood flow volume in the measurement site to cause arterialization. That is to say, when the skin is heated (to be equal to or higher than 42° C.), arterioles in a superficial vascular network in the skin receive heat stimulation, smooth muscles thereof respond to the heat stimulation, the inner diameters of the arterioles expand, and blood flow resistances thereof are decreased. As a result, the blood flow volumes flowing through the arterioles are increased and capillaries are thereby expanded, so that a blood flow rate is increased.

In nature, oxygen is consumed by tissues during passage of blood in the capillaries and arterial blood is converted into venous blood. However, in the above-described heated state, the arterial blood flows out to veins without being converted because the blood flow rate is increased and a blood flow velocity is increased. Therefore, most of the blood flowing in all of superficial intradermal blood vessels (arterioles, capillaries, and venules) is the arterial blood just under a portion around the heating unit. The magnitude of the pulsatile component is proportional to the blood flow rate of the arterial blood in the measurement site. A large pulsatile component signal for each measurement wavelength can therefore be acquired.

The reflection heating oximeter disclosed in Japanese Unexamined Patent Application Publication No. 63-23645 includes an oximeter main body and a sensor unit and both of them are connected by a wire (a lead wire). The sensor unit is configured to include an optical sensor having a light emitting element and a light receiving element, a heater, a heating body which is heated by the heater, and a thermistor measuring the temperature of the heating body. Furthermore, the oximeter main body processes the pulsatile component signals of the light absorbance of the respective measurement wavelengths, which have been detected by the sensor unit, to obtain the oxygen saturation and displays the oxygen saturation and a pulse rate on a display unit. A drive line of the light emitting element, a current supply line of the heater, a signal line of the light receiving element, and a signal line of the thermistor are put together and guided from the sensor unit as the lead wire, and are connected to the oximeter main body.

The above-described reflection heating oximeter does not take portability into consideration and it is difficult to perform continuous measurement during activity (for example, in daily life) while mounting the oximeter main body on the body. Furthermore, the configuration of the sensor unit is complicated as described above and there is the risk of increase in cost.

SUMMARY OF THE INVENTION

Preferred embodiments of the present invention provide heating oximeters that are excellent in mountability and portability, are capable of measuring oxygen saturation even during activity, and are also low cost.

A heating oximeter according to a preferred embodiment of the present invention includes a heat insulation portion that has a sheet shape and heat insulation properties, a heat generation portion that has a sheet shape and includes a resistor generating heat by energization, a first temperature detector that has a sheet shape and including a first temperature sensor detecting a temperature of the heat generation portion, and an oxygen saturation acquisition assembly having a thin plate shape, including a light emitting element and a light receiving element, and acquiring oxygen saturation in blood optically, wherein the heating oximeter is configured by stacking the oxygen saturation acquisition assembly, the first temperature detector, the heat generation portion, and the heat insulation portion in this order.

A heating oximeter according to a preferred embodiment of the present invention is preferably configured by stacking (laminating) the first temperature detector, the sheet heat generation portion, and the heat insulation portion on the oxygen saturation acquisition assembly having the thin plate shape. Therefore, the heating oximeter has a reduced thickness and weight and is excellent in mountability and portability. Furthermore, the heating oximeter can be configured by laminating the components in order and the configuration thereof is therefore relatively simple. Accordingly, the heating oximeter is also excellent in cost. As a result, the heating oximeter that is excellent in mountability and portability, is capable of measuring the oxygen saturation ($SpO_2$) even during activity, and is also low cost is provided.

In a heating oximeter according to a preferred embodiment of the present invention, it is preferable that areas of the oxygen saturation acquisition assembly, the first temperature detector, the heat generation portion, and the heat insulation portion be larger in this order.

In this case, the areas of the oxygen saturation acquisition assembly, the first temperature detector, the heat generation portion, and the heat insulation portion are larger in this order (that is, in the lamination order). Therefore, a living body (measurement site) is able to be heated from the periphery of the oxygen saturation acquisition assembly. The oxygen saturation acquisition assembly, the first temperature detector, and the heat generation portion overall are able to be covered by the heat insulation portion. Furthermore, the temperature of the heat generation portion is able to be detected while making direct contact with the heat generation portion. Therefore, the measurement site is able to be effectively heated and the temperature of the heat generation portion is able to be controlled accurately, thus acquiring the oxygen saturation accurately.

It is preferable that a heating oximeter according to a preferred embodiment of the present invention further include an adhesive portion provided on a peripheral edge portion of the heat insulation portion and having adhesive properties.

In this case, the heating oximeter further includes the adhesive portion provided on the peripheral edge portion of the heat insulation portion and having the adhesive properties. Therefore, the thin heating oximeter is able to be attached to the living body (measurement site) without interposing the adhesive portion between the oxygen saturation acquisition assembly, the first temperature detector, the heat generation portion and the living body (measurement site). Accordingly, the mountability and portability are able to be further improved without lowering measurement accuracy.

In a heating oximeter according to a preferred embodiment of the present invention, it is preferable that the first temperature detector include a second temperature sensor detecting a temperature of a living body in addition to the first temperature sensor.

In this case, the first temperature detector includes the second temperature sensor detecting the temperature of the living body in addition to the first temperature sensor. Therefore, the oxygen saturation is able to be acquired while considering the temperature of the living body (measurement site) (for example, considering whether or not a blood flow volume in the measurement site is increased to cause arterialization) in addition to the temperature of the heat generation portion, thus improving the measurement accuracy of the oxygen saturation.

It is preferable that a heating oximeter according to a preferred embodiment of the present invention further include a third temperature detector that has a sheet shape and includes a third temperature sensor detecting a temperature of a living body, wherein the third temperature sensor is arranged so as to oppose the first temperature sensor with the oxygen saturation acquisition assembly interposed between the first and third temperature sensors, and the oxygen saturation acquisition assembly measures a deep body temperature of the living body based on a detection value by the first temperature sensor and a detection value by the third temperature sensor.

In this case, the third temperature sensor is opposite the first temperature sensor with the oxygen saturation acquisition assembly interposed therebetween and the deep body temperature of the living body (at a measurement site) is measured based on the detection value (which is a temperature of the heat generation portion) by the first temperature sensor and the detection value (temperature of the measurement site) by the third temperature sensor. Therefore, the deep body temperature of the living body is able to be measured accurately. Accordingly, the oxygen saturation is able to be measured while considering the deep body temperature of the living body (for example, considering whether or not the blood flow volume in the measurement site is increased to cause arterialization), thus improving the measurement accuracy of the oxygen saturation.

In a heating oximeter according to a preferred embodiment of the present invention, it is preferable that a resistance value of the heat generation portion be increased in accordance with increase in the temperature.

In this case, the resistance value of the heat generation portion is increased in accordance with the increase in the temperature. Therefore, when the temperature is increased, a current value flowing through the heat generation portion is decreased, the heat generation amount is decreased, and the temperature is decreased. On the other hand, when the temperature is decreased, the resistance value is decreased, the current value flowing through the heat generation portion is increased, the heat generation amount is increased, and the temperature is increased again. That is to say, an autonomous temperature adjustment function is exerted such that the temperature of the heat generation portion is in a predetermined range. Therefore, for example, the current value which is made to flow through the heat generation portion needs not to be externally adjusted (F/B-controlled) in accordance with the temperature of the heat generation portion. Circuitry and/or a processor (controller) turning ON/OFF electric power to be applied are not required with the above-described autonomous temperature adjustment function, thus further reducing cost.

According to preferred embodiments of the present invention, heating oximeters that are excellent in mountability and portability, are capable of measuring oxygen saturation ($SpO_2$) even during activity, and are low cost are able to be provided.

The above and other elements, features, steps, characteristics and advantages of the present invention will become more apparent from the following detailed description of the preferred embodiments with reference to the attached drawings.

DETAILED DESCRIPTION OF THE PREFERRED EMBODIMENTS

Figure 1A:
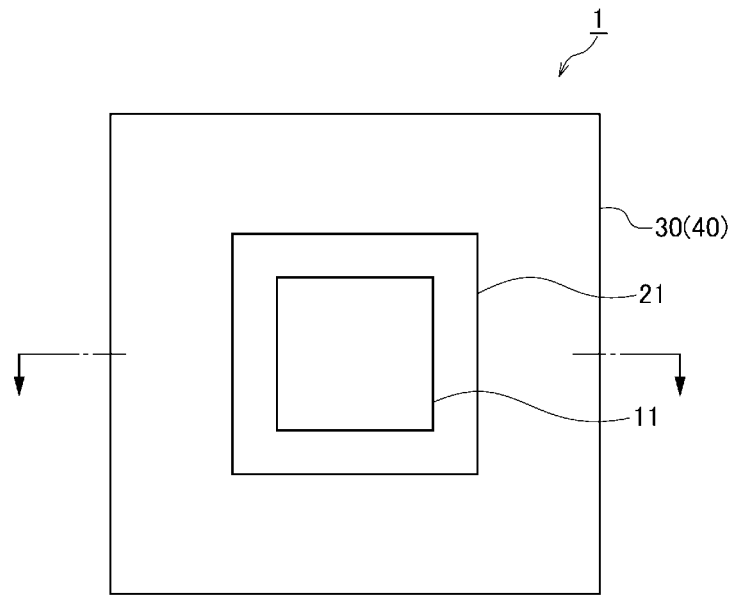
FIGS. 1A and 1B are a plan view (FIG. 1A) and a longitudinal cross-sectional view (FIG. 1B) of a heating oximeter according to a first preferred embodiment of the present invention.

Hereinafter, preferred embodiments of the present invention will be described with reference to the accompanying drawings. It should be noted that the same reference numerals denote the same or equivalent portions in the drawings. In the respective drawings, the same reference numerals denote the same elements and overlapped description thereof is omitted.

First Preferred Embodiment

Figure 1B:
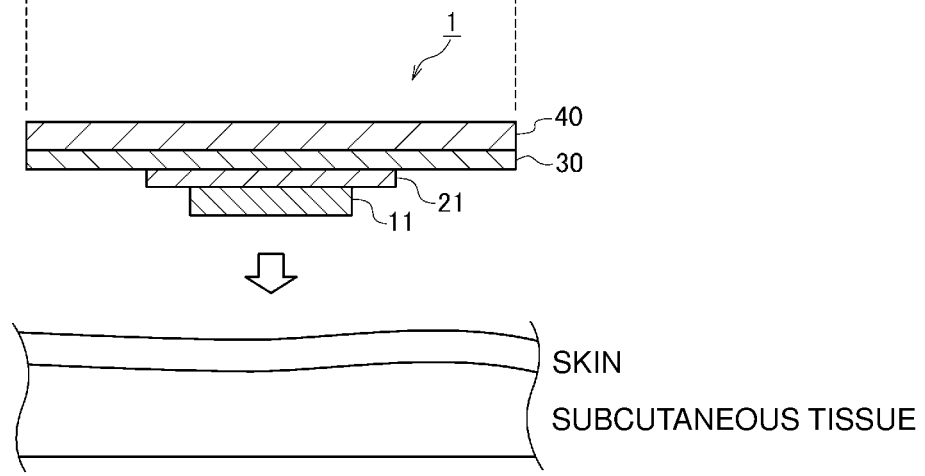
Figure 2:
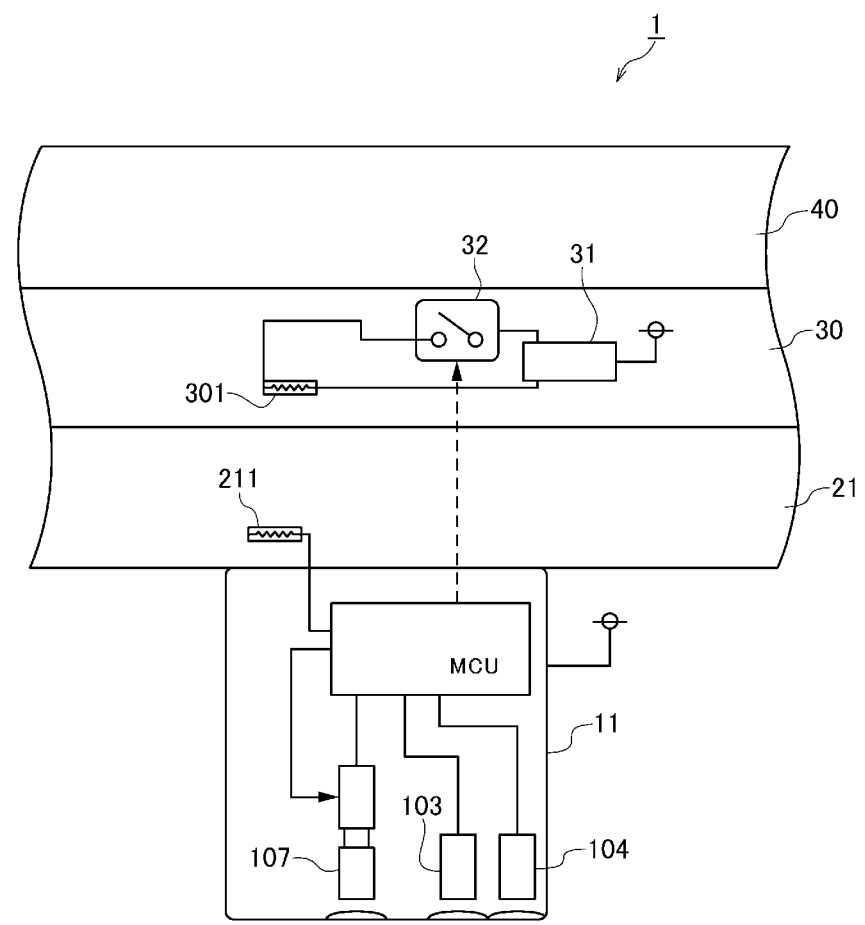
FIG. 2 is a view illustrating a main component of the heating oximeter according to the first preferred embodiment of the present invention in an enlarged manner.
Figure 3:
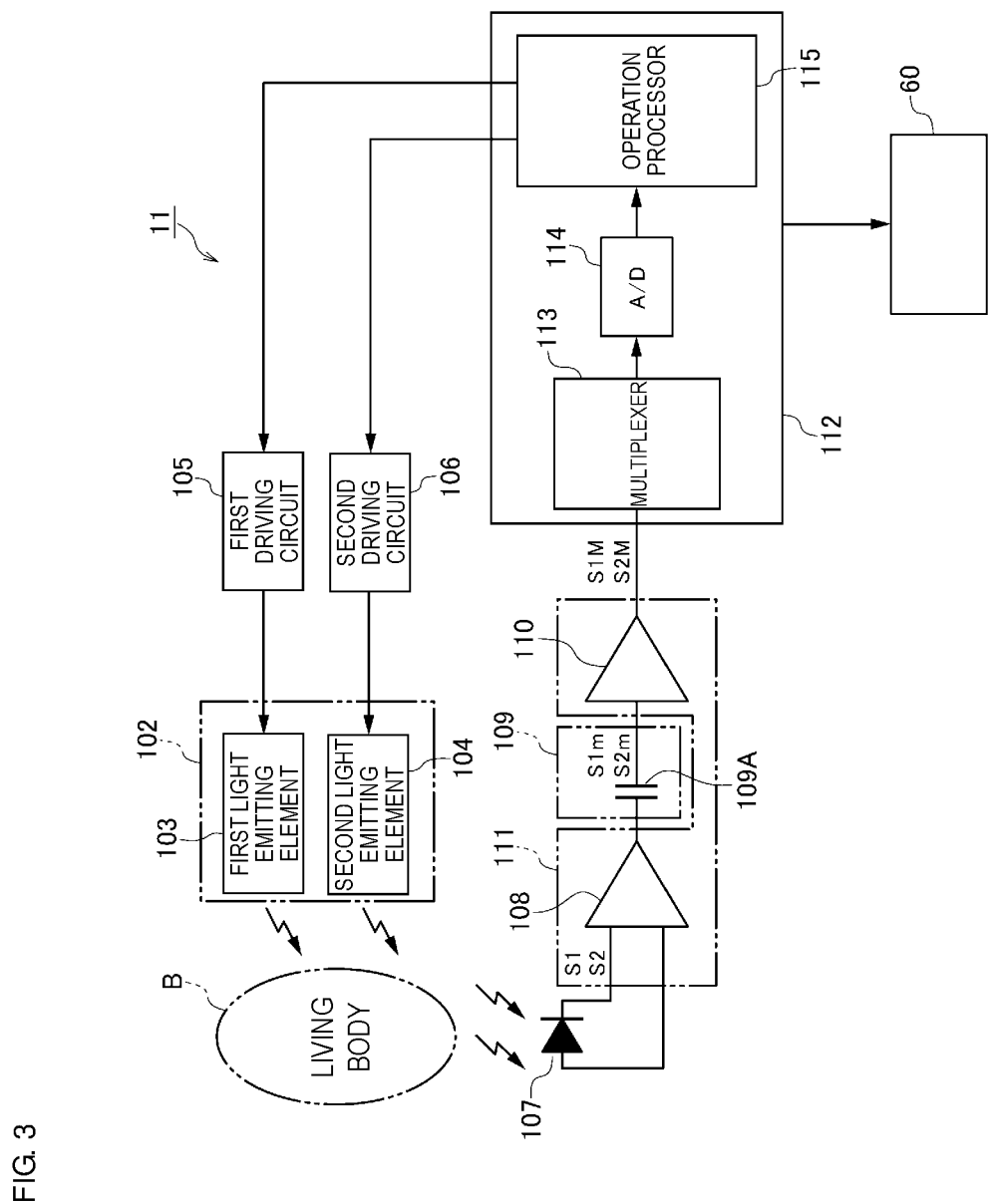
FIG. 3 is a block diagram illustrating the configuration of an oxygen saturation acquisition assembly constituting the heating oximeter according to the first preferred embodiment of the present invention.

First, the configuration of a heating pulse oximeter (hereinafter, simply referred to as a "heating oximeter") 1 according to a first preferred embodiment will be described with reference to FIG. 1 to FIG. 3. FIG. 1A is a plan view and FIG. 1B is a longitudinal cross-sectional view of the heating oximeter 1. FIG. 2 is a view illustrating a main component of the heating oximeter 1 in an enlarged manner. FIG. 3 is a block diagram illustrating the configuration of an oxygen saturation acquisition assembly 11 of the heating oximeter 1.

The heating oximeter 1 has a heating function of heating a measurement site, increasing a blood flow volume in the measurement site to cause arterialization, and optically measuring oxygen saturation (e.g., a presence ratio between oxygenated hemoglobin and reduced hemoglobin) using light absorption characteristics of hemoglobin (i.e., oxygenated hemoglobin and reduced hemoglobin) in blood, specific details of this will be described later. In particular, the heating oximeter 1 is excellent in mountability and portability, is capable of continuously measuring the oxygen saturation even during activity, and is also excellent in being low cost.

Therefore, the heating oximeter 1 preferably includes a heat insulation portion 40, a heat generation portion 30, a first temperature detector 21, and the oxygen saturation acquisition assembly 11. The heating oximeter 1 is preferably configured by stacking (laminating) these respective components in the order of the oxygen saturation acquisition assembly 11, the first temperature detector (first temperature detection layer) 21, the heat generation portion (heat generation layer) 30, and the heat insulation portion (heat insulation layer) 40.

The heat insulation portion 40 preferably has, for example, a rectangular thin sheet shape. It should be noted that the shape of the heat insulation portion 40 is not limited to the rectangular shape and may be, for example, a circular shape or the like. The heat insulation portion 40 is made of a material having heat insulation properties, for example, preferably a polyethylene foamed body, a urethane foamed body, or the like. The heat insulation portion 40 preferably has flexibility so as to follow a shape and motion of a body surface. The thickness of the heat insulation portion 40 is preferably, for example, approximately 0.1 mm to several mm in consideration of the heat insulation properties and the flexibility. The area of the heat insulation portion 40 is preferably equal to or larger than the areas of the heat generation portion 30, the first temperature detector 21, and the oxygen saturation acquisition assembly 11 and the heat insulation portion 40 is provided so as to cover them overall.

The heat generation portion 30 preferably has, for example, a rectangular thin sheet shape and includes a resistor generating heat by energization. It should be noted that the shape of the heat generation portion 30 is not limited to the rectangular shape and may be, for example, a circular shape or the like. To be more specific, the heat generation portion 30 is configured to be used as a sheet-shaped heating element by applying current to the resistor. Examples of the configuration of the heat generation portion 30 include the configuration in which the sheet (heat generation portion 30) itself is a heat generation resistor, the configuration in which a heat generation resistor is patterned (or applied) in, for example, a meander form onto the upper surface and/or the lower surface of the sheet (or inside the sheet), and the configuration in which a plurality of resistors (resistive elements) are arranged in an array on the upper surface and/or lower surface of the sheet. The area of the heat generation portion 30 is equal to or smaller than the area of the heat insulation portion 40 and is larger than the area of the first temperature detector 21, and the heat generation portion 30 is disposed between the heat insulation portion 40 and the first temperature detector 21.

A thin battery 31 having a sheet shape and including a switching element 32 (for example, a semiconductor element such as a transistor) turning ON/OFF electric power (i.e., electric current) is applied to a resistor 301 from the thin battery 31 are provided on the surface of or inside the heat generation portion 30. The switching element 32 is connected to the oxygen saturation acquisition assembly 11 and the current flowing through the heat generation portion 30 (resistor 301) is controlled by the oxygen saturation acquisition assembly 11 (that is to say, the temperature thereof is adjusted). It should be noted that the oxygen saturation acquisition assembly 11 may include the thin battery 31 and the switching element 32 if so desired.

The first temperature detector 21 preferably has, for example, a rectangular sheet shape and includes a first temperature sensor 211 detecting the temperature of the heat generation portion 30. It should be noted that the shape of the first temperature detector 21 is not also limited to the rectangular shape and may be, for example, a circular shape or the like. The area of the first temperature detector 21 is smaller than the area of the heat generation portion 30 and is equal to or larger than the area of the oxygen saturation acquisition assembly 11, and the first temperature detector 21 is disposed between the heat generation portion 30 and the oxygen saturation acquisition assembly 11. For example, a thermistor (preferably a NPT thermistor) a resistance value of which is changed with the temperature, or the like, is preferably used as the first temperature sensor 211. The first temperature sensor 211 is connected to the oxygen saturation acquisition assembly 11 and an electric signal (voltage value) thereof in accordance with the temperature of the heat generation portion 30 is read by the oxygen saturation acquisition assembly 11.

The oxygen saturation acquisition assembly 11 has, for example, a rectangular flexible thin-plate shape (or sheet shape), includes two light emitting elements 103 and 104 emitting light of different wavelengths and a light receiving device (light receiving element) 107, and optically acquires the oxygen saturation (presence ratio between the oxygenated hemoglobin and the reduced hemoglobin). It should be noted that the shape of the oxygen saturation acquisition assembly 11 is not also limited to the rectangular shape and may be, for example, a circular shape or the like. The oxygen saturation acquisition assembly 11 reads the temperature of the heat generation portion 30, which has been detected by the first temperature detector 21 (first temperature sensor 211), and controls (F/B-controls) the current to be applied to the heat generation portion 30 (resistor 301) such that the temperature of the heat generation portion 30 is a predetermined setting temperature (that is to say, adjusts the temperature thereof). The oxygen saturation acquisition assembly 11 will be described more in detail with reference to FIG. 3.

A light emitting device 102 is configured by the first and second light emitting elements 103 and 104 outputting light of a first wavelength band and light of a second wavelength band, which are different from each other, respectively. In the present preferred embodiment, light emitting diodes (LED) are used as the first and second light emitting elements 103 and 104. The first light emitting element 103 emits red light in a band of, for example, about 700 nm, which has a high light absorption coefficient by the reduced hemoglobin, and the second light emitting element 104 emits infrared light in a band of, for example, about 900 nm, which has a high light absorption coefficient by the oxygenated hemoglobin.

First and second driving circuits 105 and 106 are respectively connected to the first and second light emitting elements 103 and 104. The first and second light emitting elements 103 and 104 emit light in a flashing manner in accordance with driving signals supplied from the first and second driving circuits 105 and 106, respectively. The first driving circuit 105 supplies the driving signal pulse of which has been modulated with a predetermined frequency f.

The second driving circuit 106 preferably is configured in substantially the same manner as the first driving circuit 105. Therefore, the second driving circuit 106 supplies, to the second light emitting element 104, the driving signal pulse of which has been modulated with the predetermined frequency f, which is the same as that of the first driving circuit 105, and causes the second light emitting element 104 to emit light in the flashing manner. It should be noted that in this case, the first and second light emitting elements 103 and 104 emit light at different timings (for example, alternately).

When the light receiving device 107 receives the light components of the first and second wavelength bands in an isolation manner, the first and second light emitting elements 103 and 104 may emit light together in synchronization with each other. It should be noted that surface emitting laser (VCSEL) or laser diodes (LD) may be used as the first and second light emitting elements 103 and 104, for example.

The light receiving device 107 is preferably defined by, for example, a light receiving element such as a photo diode (PD) and performs photoelectric conversion on received light into an electric signal for output. To be specific, the light receiving device 107 receives light that has been emitted from the light emitting elements 103 and 104 and has been reflected by or has passed through a living body B, converts the received light into first and second detection signals S1 and S2, and outputs these detection signals S1 and S2 to a previous-stage amplifier 108. In this case, the first detection signal S1 is a signal corresponding to light of the first wavelength band and the second detection signal S2 is a signal corresponding to light of the second wavelength band.

It should be noted that the light receiving device 107 may include, for example, a photo transistor as the light receiving element. The light receiving device 107 may include a single light receiving element or may include a plurality of light receiving elements receiving light components of different wavelength bands by including, for example, an optical filter or the like.

The previous-stage amplifier 108 is preferably configured using, for example, an operation amplifier, and an input terminal thereof is connected to the light receiving device 107. The previous-stage amplifier 108 amplifies the detection signals S1 and S2 output from the light receiving device 107 and outputs them to a filter circuit 109.

The filter circuit 109 includes a capacitor 109A as a coupling capacitor connected between the previous-stage amplifier 108 and a next-stage amplifier 110. The filter circuit 109 functions as a high pass filter capable of transmitting a signal with the predetermined frequency f with which the light emitting elements 103 and 104 emit light in the flashing manner and signals having higher frequencies than that of the signal.

The first and second detection signals S1 and S2 are provided by amplitude modulation of the signals with the predetermined frequency f because the light emitting device 102 emits light in the flashing manner with the predetermined frequency f. In this case, the capacitor 109A blocks signals with lower frequencies than the predetermined frequency f and the filter circuit 109 therefore extracts modulated signals S1$m$ and S2$m$ provided by the amplitude modulation with the predetermined frequency f from the first and second detection signals S1 and S2 for output.

The next-stage amplifier 110 is an amplifier that amplifies the modulated signals S1$m$ and S2$m$. The next-stage amplifier 110 is preferably, for example, an operation amplifier, and defines an amplification circuit 111 together with the previous-stage amplifier 108. The next-stage amplifier 110 is connected to the output side of the filter circuit 109, amplifies the first and second modulated signals S1$m$ and S2$m$, and outputs first and second modulated signals S1M and S2M.

A processing circuit 112 is preferably defined by a multiplexer 113, an AD converter 114, and an operation processor 115. The multiplexer 113 connects the next-stage amplifier 110 to the AD converter 114. With this configuration, the first and second modulated signals S1M and S2M output from the next-stage amplifier 110 are input to the AD converter 114 with the multiplexer 113 interposed therebetween.

The AD converter 114 converts the first and second modulated signals S1M and S2M from analog signals to digital signals. In this case, the AD converter 114 converts, for example, only positive-side signals of the first and second modulated signals S1M and S2M to digital values.

The operation processor 115 is preferably provided by, for example, a microcomputer or the like, calculates DC components S1$d$ and S2$d$ and AC components S1$a$ and S2$a$ of the first and second detection signals S1 and S2 based on the first and second modulated signals S1M and S2M output from the AD converter 114, and obtains a light absorption ratio R12 of the living body B. The operation processor 115 generates living body information such as the oxygen saturation, acceleration pulse waves, and a pulse rate based on the first and second detection signals S1 and S1 in addition to the light absorption ratio R12.

The oxygen saturation acquisition assembly 11 accommodates therein a wireless communication unit 60 that transmits the living body information such as the measured oxygen saturation to an external apparatus. It should be noted that measurement data such as the acquired oxygen saturation is transmitted to, for example, a personal computer (PC), a smart phone or a portable music player having a display, or the like with the wireless communication unit 60 interposed therebetween. In this case, it is preferable that data such as the measurement date and time be also transmitted in addition to a measurement result and a detection result.

Next, a usage method of the heating oximeter 1 will be described. When the oxygen saturation and the like are measured using the heating oximeter 1, the heating oximeter 1 is attached to (mounted on), for example, the arm, the chest, or the head of a user.

With the attachment, the temperature of the heat generation portion 30, which has been detected by the first temperature detector 21 (first temperature sensor 211), is read and the current that is applied to the heat generation portion 30 (resistor 301) is controlled (F/B-controlled) such that the temperature of the heat generation portion 30 is the predetermined setting temperature (that is to say, the temperature thereof is adjusted). The pulsatile component is able to be detected and the oxygen saturation is able to be measured by thus heating the measurement site and increasing the blood flow volume in the measurement site to cause arterialization. That is to say, when the skin is heated, the arterioles in the superficial vascular network in the skin receive heat stimulation, the smooth muscles thereof respond to the heat stimulation, the inner diameters of the arterioles expand, and blood flow resistances thereof are decreased. As a result, the blood flow volume flowing through the arterioles is increased and the capillaries are thereby expanded, so that the blood flow rate is increased. In nature, oxygen is consumed by tissues during passage of blood in the capillaries and arterial blood is converted into venous blood. However, in the above-described heated state, the arterial blood flows out to veins without being converted because the blood flow rate is increased and a blood flow velocity is increased. Therefore, most of the blood flowing in all of superficial intradermal blood vessels (arterioles, capillaries, and venules) is the arterial blood just under a portion around the heating unit.

Thereafter, light in the vicinity of red light having the high light absorption coefficient by the reduced hemoglobin is output by the light emitting element 103 and light in the vicinity of infrared light having the high light absorption coefficient by the oxygenated hemoglobin is output by the light emitting element 104. The oxygen saturation in blood based on the presence ratio between the oxygenated hemoglobin and the reduced hemoglobin is then acquired. The method for acquiring the oxygen saturation has been described in detail above and detail description thereof is therefore omitted herein. In this manner, the user can acquire and measure the oxygen saturation and the like only by mounting the heating oximeter 1 (attaching it to the skin). The living body information such as the acquired and measured oxygen saturation is transmitted to the external apparatus (for example, the smart phone or the like) by the wireless communication unit 60.

As described in detail above, with the present preferred embodiment, the heating oximeter 1 is preferably provided by stacking (laminating) the sheet first temperature detector 21, the sheet heat generation portion 30, and the sheet heat insulation portion 40 on the oxygen saturation acquisition assembly 11. Therefore, the heating oximeter 1 is able to be reduced in thickness and weight and is able to be made excellent in the mountability and portability. Furthermore, the heating oximeter 1 can be configured by laminating the components in sequence and the configuration thereof is therefore relatively simple. Accordingly, the manufacturing cost and the like is able to be reduced. As a result, the heating oximeter 1 that is excellent in the mountability and portability, is capable of stably measuring the oxygen saturation ($SpO_2$) even during activity, and also has low cost is able to be provided.

Furthermore, with the present preferred embodiment, the areas of the oxygen saturation acquisition assembly 11, the first temperature detector 21, the heat generation portion 30, and the heat insulation portion 40 are larger in this order (that is, in the lamination order). Therefore, the living body (measurement site) is able to be heated from the periphery of the oxygen saturation acquisition assembly 11. Moreover, the oxygen saturation acquisition assembly 11, the first temperature detector 21, and the heat generation portion 30 overall is able to be covered by the heat insulation portion 40. Furthermore, the temperature of the heat generation portion 30 is able to be detected while making direct contact with the heat generation portion 30. Therefore, the measurement site is able to be effectively heated and the temperature of the heat generation portion 30 is able to be controlled accurately, thus acquiring the oxygen saturation accurately for a short period of time. In addition, acquisition conditions of the oxygen saturation are able to be stabilized.

Variation on First Preferred Embodiment

Figure 4:
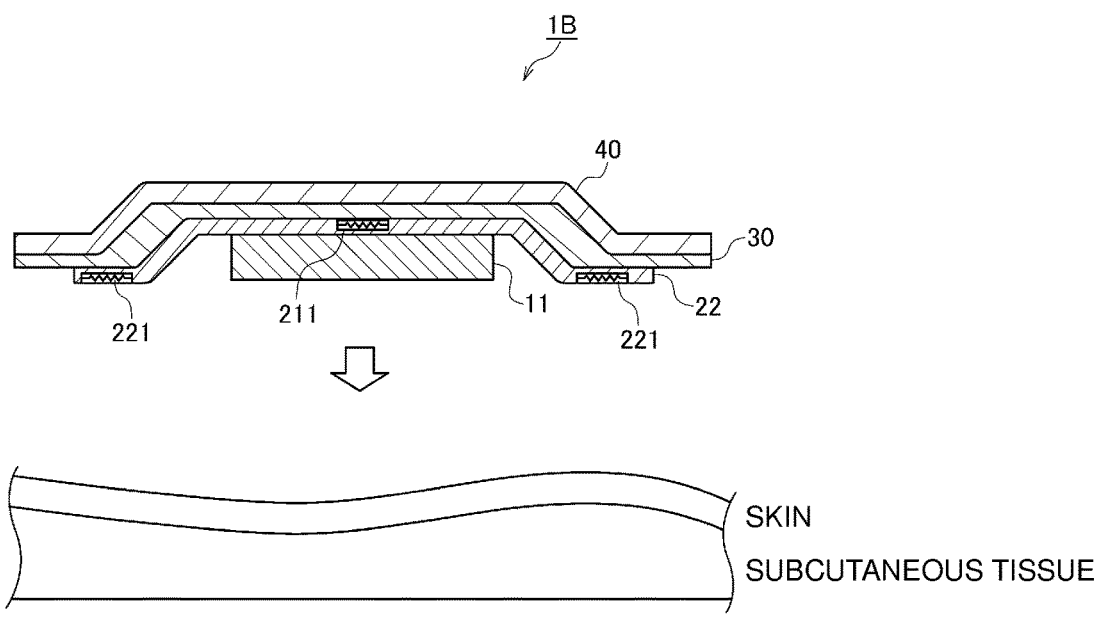
FIG. 4 is a longitudinal cross-sectional view of a heating oximeter according to a variation on the first preferred embodiment of the present invention.

Next, a heating oximeter 1B according to a variation on the first preferred embodiment will be described with reference to FIG. 4. Description of the same or similar configurations as or to those in the above-described first preferred embodiment is simplified or omitted and different points are mainly described. FIG. 4 is a longitudinal cross-sectional view of the heating oximeter 1B. It should be noted that the same reference numerals denote the same or equivalent components as or to those in the first preferred embodiment in FIG. 4.

The heating oximeter 1B is different from the heating oximeter 1 (first temperature detector 21) according to the above-described first preferred embodiment in a point that a second temperature detector 22 preferably includes a second temperature sensor 221 measuring the temperature of a living body (skin) in addition to the first temperature sensor 211 detecting the temperature of the heat generation portion 30. It should be noted that other configurations are the same as or similar to those of the above-described heating oximeter 1 and detail description thereof is therefore omitted herein.

To be more specific, the second temperature detector 22 preferably extends such that a peripheral edge portion thereof makes contact with the living body (skin) and the second temperature sensor 221 that detects the temperature of the living body (skin) is disposed in the peripheral edge portion. As the second temperature sensor 221, an NPT thermistor or the like is preferably used in the same manner as the above-described first temperature sensor 211. The second temperature sensor 221 is also connected to the oxygen saturation acquisition assembly 11 and an electric signal (voltage value) thereof in accordance with the temperature of the living body (skin) is read by the oxygen saturation acquisition assembly 11.

With the variation, the second temperature detector 22 includes the second temperature sensor 221 measuring the temperature of the living body (skin) in addition to the first temperature sensor 211 detecting the temperature of the heat generation portion 30. Therefore, the oxygen saturation is able to be measured while considering the temperature of the living body (skin) (for example, considering whether or not the blood flow volume in the measurement site is increased to cause arterialization) in addition to the temperature of the heat generation portion 30, thus improving the measurement accuracy of the oxygen saturation.

Second Preferred Embodiment

Figure 5:
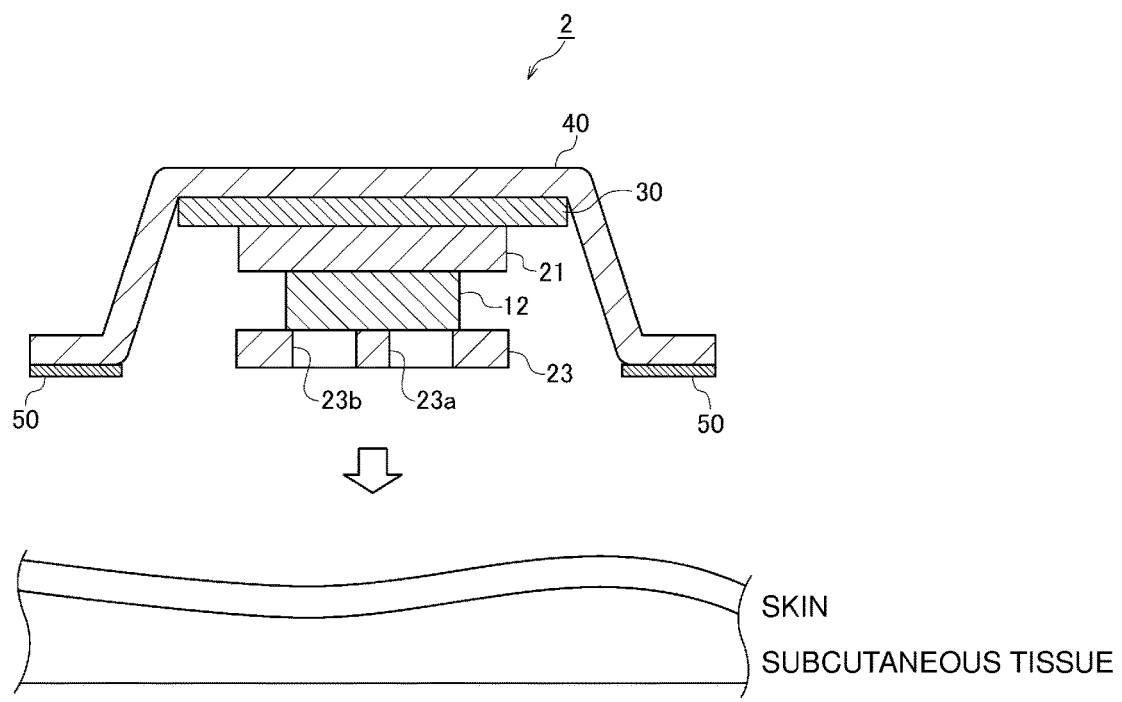
FIG. 5 is a longitudinal cross-sectional view of the heating oximeter according to a second preferred embodiment of the present invention.
Figure 6:
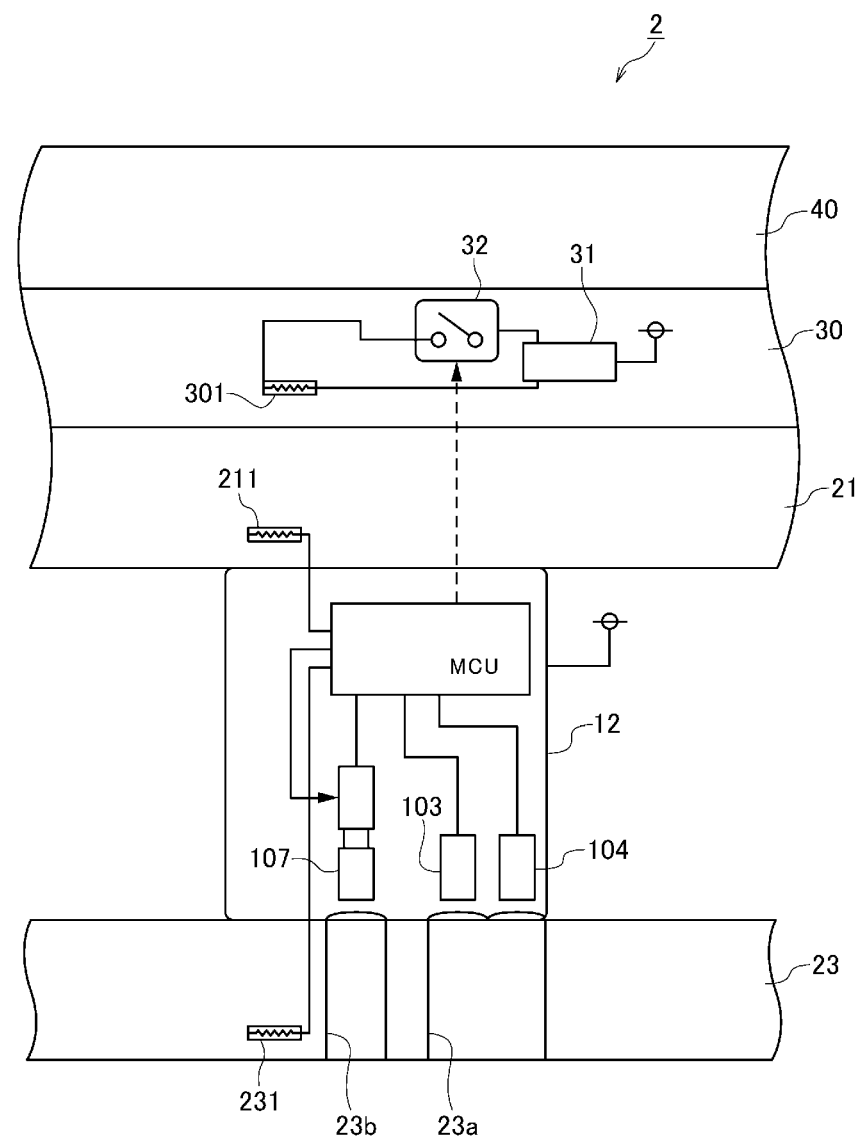
FIG. 6 is a view illustrating a main component of the heating oximeter according to the second preferred embodiment of the present invention in an enlarged manner.

Next, a heating oximeter 2 according to a second preferred embodiment will be described with reference to FIGS. 5 and 6. Description of the same or similar configurations as or to those in the above-described first preferred embodiment is simplified or omitted and different points are mainly described. FIG. 5 is a longitudinal cross-sectional view of the heating oximeter 2. FIG. 6 is a view illustrating a main component of the heating oximeter 2 in an enlarged manner. It should be noted that the same reference numerals denote the same or equivalent components as or to those in the first preferred embodiment in FIGS. 5 and 6.

The heating oximeter 2 is different from the heating oximeter 1 according to the above-described first preferred embodiment in a point that it further includes a third temperature detector 23 and in a point that it includes an oxygen saturation acquisition assembly 12 instead of the oxygen saturation acquisition assembly 11. It should be noted that other configurations are the same as or similar to those of the above-described heating oximeter 1 and detail description thereof is therefore omitted herein.

The third temperature detector 23 preferably has, for example, a rectangular thin sheet shape and includes a third temperature sensor 231 detecting the temperature of the living body (measurement site). It should be noted that the shape of the third temperature detector 23 is not also limited to the rectangular shape and may be, for example, a circular shape or the like. The third temperature sensor 231 (third temperature detector 23) is arranged so as to oppose the first temperature sensor 211 (first temperature detector 21) with the oxygen saturation acquisition assembly 12 interposed therebetween. As the third temperature sensor 231, an NPT thermistor or the like is preferably used in the same manner as the above-described first temperature sensor 211. The third temperature sensor 231 is connected to the oxygen saturation acquisition assembly 12 and an electric signal (voltage value) thereof in accordance with the temperature of the living body (measurement site) is read by the oxygen saturation acquisition assembly 12.

Furthermore, the third temperature detector 23 includes through-holes 23a and 23b provided at positions corresponding to the light emitting device 102 (light emitting elements 103 and 104) and the light receiving device 107 provided in the oxygen saturation acquisition assembly 12, respectively. Light emission of the measurement light by the light emitting device 102 (light emitting elements 103 and 104) and light reception of the measurement light by the light receiving device 107 are performed while causing the light to pass through the through-holes 23a and 23b.

The oxygen saturation acquisition assembly 12 measures a deep body temperature of the living body (measurement site) based on a detection value (temperature of the heat generation portion 30) by the first temperature sensor 211 and a detection value (temperature of the measurement site) by the third temperature sensor 231. To be more specific, heat dissipation from a body surface is eliminated apparently by applying a heat flow compensation method, thus eliminating heat flow to the body surface from a body inner portion. With this, the body surface and the body inner portion are made into thermal equilibrium states. The body surface temperature is measured in this state, thus measuring the same temperature as that of the deep portion.

That is to say, the two temperature sensors, that is, the first temperature sensor 211 and the third temperature sensor 231 are arranged with the oxygen saturation acquisition assembly interposed therebetween and the body surface temperature is detected by the third temperature sensor 231 and the temperature of the heat generation portion 30 is detected by the first temperature sensor 211. The deep body temperature is able to be measured noninvasively by controlling the current which is made to flow through the heat generation portion 30 such that the temperature difference therebetween is zero.

The oxygen saturation acquisition assembly 12 acquires the oxygen saturation while considering the detected deep body temperature (for example, considering whether or not the blood flow volume in the measurement site is increased to cause arterialization).

It should be noted that in the heating oximeter 2, a thin film-shaped adhesive portion (adhesive layer) 50 having adhesive properties (adhesiveness) is mounted on the peripheral edge portion of the heat insulation portion 40. It is preferable that the adhesive portion 50 be made of a material having biocompatibility. The heating oximeter 2 is able to be easily attached to the living body (measurement site) with adhesive force of the adhesive portion 50.

With the present preferred embodiment, the third temperature sensor 231 is arranged to oppose the first temperature sensor 211 with the oxygen saturation acquisition assembly 12 interposed therebetween and the deep body temperature of the living body is measured based on the detection value (the temperature of the heat generation portion 30) by the first temperature sensor 211 and the detection value (temperature of the measurement site) by the third temperature sensor 231. Therefore, the deep body temperature of the living body is able to be measured accurately. Accordingly, the oxygen saturation is able to be measured while considering the deep body temperature of the living body (measurement site) (for example, considering whether or not the blood flow volume in the measurement site is increased to cause arterialization), thus improving the measurement accuracy of the oxygen saturation.

Furthermore, with the present preferred embodiment, the adhesive portion 50 having the adhesive properties is preferably provided on the peripheral edge portion of the heat insulation portion 40. Therefore, the thin heating oximeter 2 is able to be attached to the living body (measurement site) without interposing the adhesive portion 50 between the third temperature detector 23, the oxygen saturation acquisition assembly 12, the first temperature detector 21, and the heat generation portion 30 and the living body (measurement site). Accordingly, the mountability and portability are able to be further improved without lowering the measurement accuracy.

Third Preferred Embodiment

Figure 7:
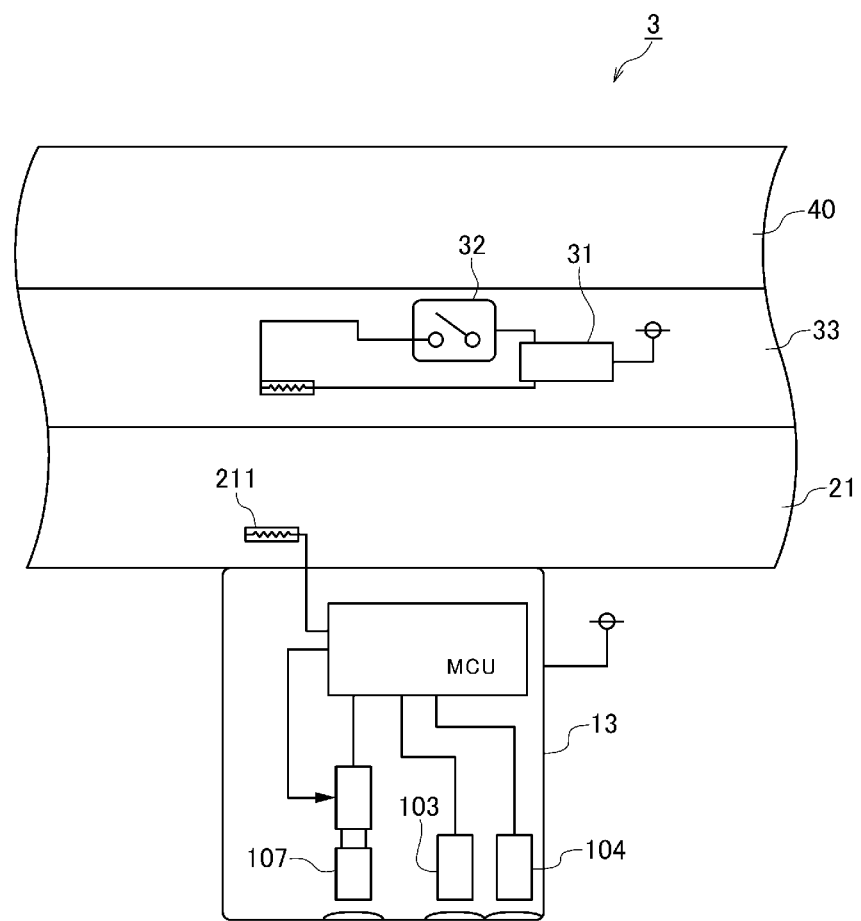
FIG. 7 is a longitudinal cross-sectional view of a heating oximeter according to a third preferred embodiment of the present invention.

Next, a heating oximeter 3 according to a third preferred embodiment of the present invention will be described with reference to FIG. 7. Description of the same or similar configurations as or to those in the above-described first preferred embodiment is simplified or omitted and different points are mainly described. FIG. 7 is a longitudinal cross-sectional view of the heating oximeter 3. It should be noted that the same reference numerals denote the same or equivalent components as or to those in the first preferred embodiment in FIG. 7.

The heating oximeter 3 is different from the heating oximeter 1 according to the above-described first preferred embodiment in a point that it includes a heat generation portion 33 instead of the heat generation portion 30. It should be noted that other configurations are the same as or similar to those of the above-described heating oximeter 1 and detail description thereof is therefore omitted herein.

A resistance value of the heat generation portion 33 is increased in accordance with increase in the temperature. Therefore, when the temperature of the heat generation portion 33 is increased, a value of current flowing through the heat generation portion 33 is decreased, the heat generation amount is decreased, and the temperature is decreased. On the other hand, when the temperature of the heat generation portion 33 is decreased, the resistance value is decreased, the value of current flowing through the heat generation portion 33 is increased, the heat generation amount is increased, and the temperature is increased again. That is to say, an autonomous temperature adjustment function is exerted such that the temperature of the heat generation portion 33 is in a predetermined range.

As the heat generation portion 33, for example, a member made by mixing resin and resistive powder, or the like can be used. In this case, when the temperature is increased, the resin is softened and the total resistance value as a sheet (heat generation portion 33) is thus increased. As a result, the flow of current is reduced, the heat generation amount is decreased, and the temperature is decreased as described above.

With the present preferred embodiment, the resistance value of the heat generation portion 33 is increased in accordance with the increase in the temperature. Therefore, when the temperature is increased, the value of current flowing through the heat generation portion 33 is decreased, the heat generation amount is decreased, and the temperature is decreased. On the other hand, when the temperature is decreased, the resistance value is decreased, the value of current flowing through the heat generation portion 33 is increased, the heat generation amount is increased, and the temperature is increased again. That is to say, the autonomous temperature adjustment function is exerted such that the temperature of the heat generation portion 33 is in the predetermined range. Therefore, for example, the value of current which is made to flow through the heat generation portion 33 needs not to be adjusted (F/B-controlled) in accordance with the temperature of the heat generation portion 33. As a result, a circuit and processing (control) for turning ON/OFF electric power to be applied are not required, thus further reducing cost.

Although the preferred embodiments of the present invention have been described above, the invention is not limited by the above-described preferred embodiments and various variations can be made. For example, the shapes, sizes, materials, and the like of the oxygen saturation acquisition assemblies 11, 12, and 13, the first, second, third temperature detectors 21, 22, and 23, the heat generation portions 30 and 33, the heat insulation portion 40, and the adhesive portion 50 are not limited to those in the above-described preferred embodiments and can be arbitrarily set in accordance with requirements and the like.

While preferred embodiments of the present invention have been described above, it is to be understood that variations and modifications will be apparent to those skilled in the art without departing from the scope and spirit of the present invention. The scope of the present invention, therefore, is to be determined solely by the following claims.

What is claimed is:

1. A heating oximeter comprising:
    a heat insulation portion that has a sheet shape and heat insulation properties;
    a heat generation portion that has a sheet shape and includes a resistor to generate heat by energization;
    a first temperature detector that has a sheet shape and includes a first temperature sensor to detect a temperature of the heat generation portion; and
    an oxygen saturation acquisition assembly having a thin plate shape, including a light emitting element and a light receiving element, to acquire oxygen saturation in blood optically; wherein
    the heating oximeter is defined by a stacked structure including the oxygen saturation acquisition assembly, the first temperature detector, the heat generation portion, and the heat insulation portion stacked in this order.

2. The heating oximeter according to claim 1, wherein areas of the oxygen saturation acquisition assembly, the first temperature detector, the heat generation portion, and the heat insulation portion increase in size in this order.

3. The heating oximeter according to claim 1, further comprising an adhesive portion provided on a peripheral edge portion of the heat insulation portion and having adhesive properties.

4. The heating oximeter according to claim 1, wherein the first temperature detector includes a second temperature sensor to detect a temperature of a living body in addition to the first temperature sensor to detect the temperature of the heat generation portion.

5. The heating oximeter according to claim 1, further comprising
    a third temperature detector having a sheet shape and including a third temperature sensor to detect a temperature of a living body; wherein
    the third temperature sensor opposes the first temperature sensor with the oxygen saturation acquisition assembly interposed between the first and third temperature sensors; and
    the oxygen saturation acquisition assembly measures a deep body temperature of the living body based on a detection value by the first temperature sensor and a detection value by the third temperature sensor.

6. The heating oximeter according to claim 5, wherein the third temperature detector includes a through-hole defined at a position corresponding to the light emitting element.

7. The heating oximeter according to claim 5, further comprising a thin battery having a sheet shape and including a switching element provided on a surface of or inside the heat generation portion.

8. The heating oximeter according to claim 5, wherein the light emitting element includes two light emitting elements emitting light of different wavelengths.

9. The heating oximeter according to claim 8, wherein the light of different wavelengths includes red light in a band of 700 nm and infrared light in a band of about 900 nm.

10. The heating oximeter according to claim 8, further comprising first and second driving circuits each respectively connected to a respective one of the two light emitting elements to drive the two light emitting elements in a flashing manner in accordance with driving signals supplied from the first and second driving circuits.

11. The heating oximeter according to claim 10, wherein the first and second driving circuits drive the two light emitting elements at a same predetermined frequency and at different timings.

12. The heating oximeter according to claim 1, wherein a resistance value of the heat generation portion is increased in accordance with increase in the temperature.

13. The heating oximeter according to claim 12, wherein the light emitting element includes two light emitting elements emitting light of different wavelengths.

14. The heating oximeter according to claim 1, further comprising a thin battery having a sheet shape and including a switching element provided on a surface of or inside the heat generation portion.

15. The heating oximeter according to claim 1, wherein the first temperature sensor is a thermistor.

16. The heating oximeter according to claim 1, wherein the light emitting element includes two light emitting elements emitting light of different wavelengths.

17. The heating oximeter according to claim 16, wherein the light of different wavelengths includes red light in a band of 700 nm and infrared light in a band of about 900 nm.

18. The heating oximeter according to claim 16, further comprising first and second driving circuits each respectively connected to a respective one of the two light emitting elements to drive the two light emitting elements in a flashing manner in accordance with driving signals supplied from the first and second driving circuits.

19. The heating oximeter according to claim 18, wherein the first and second driving circuits drive the two light emitting elements at a same predetermined frequency and at different timings.

20. The heating oximeter according to claim 1, further comprising a thin film-shaped adhesive portion having adhesive properties mounted on a peripheral edge portion of the heat insulation portion.

* * * * *